US010278879B1

United States Patent
Day

(10) Patent No.: US 10,278,879 B1
(45) Date of Patent: May 7, 2019

(54) ARM SUPPORT SYSTEM

(71) Applicant: Steven Jason Day, Arvada, CO (US)

(72) Inventor: Steven Jason Day, Arvada, CO (US)

(*) Notice: Subject to any disclaimer, the term of this patent is extended or adjusted under 35 U.S.C. 154(b) by 213 days.

(21) Appl. No.: 15/438,531

(22) Filed: Feb. 21, 2017

Related U.S. Application Data

(60) Provisional application No. 62/296,794, filed on Feb. 18, 2016.

(51) Int. Cl.
*A61G 13/12* (2006.01)
*A61G 7/075* (2006.01)
*A61G 7/05* (2006.01)
*A61G 13/10* (2006.01)
*A61M 5/52* (2006.01)
*A61M 5/14* (2006.01)

(52) U.S. Cl.
CPC ....... *A61G 13/1235* (2013.01); *A61G 7/0503* (2013.01); *A61G 7/075* (2013.01); *A61G 13/101* (2013.01); *A61M 5/1415* (2013.01); *A61M 5/52* (2013.01); *A61G 2210/00* (2013.01)

(58) Field of Classification Search
CPC ....................................................... A61G 13/12

USPC ..................................... 5/601, 721–724, 646
See application file for complete search history.

(56) References Cited

U.S. PATENT DOCUMENTS

| 7,017,209 B1* | 3/2006 | De Jong | A61B 6/0442 378/20 |
| 2009/0158526 A1* | 6/2009 | Kinmon | A61B 5/0555 5/601 |

* cited by examiner

*Primary Examiner* — Fredrick C Conley
(74) *Attorney, Agent, or Firm* — Plager Schack LLP

(57) ABSTRACT

An arm support system is configured to hold a patient's arm straight during administration of IV fluids in a radiological procedure. The arm support system further includes a base attached to a plurality of straps for securing the base to a table or a bed with the plurality of straps. The base is further attached to an upright unit that, in turn, is attached to an IV upright member and to a right triangular support. Furthermore, a telescoping arm member and a telescoping IV member is attached to the upright member and the IV upright member, respectively. Then, the telescoping IV member is attached to a plurality of IV loops while the telescoping arm member is attached to a handle with a handle grip on both sides. A patient holds onto the handle grips that keeps the patient's arms straight while administrating IV during the radiological procedure.

6 Claims, 4 Drawing Sheets

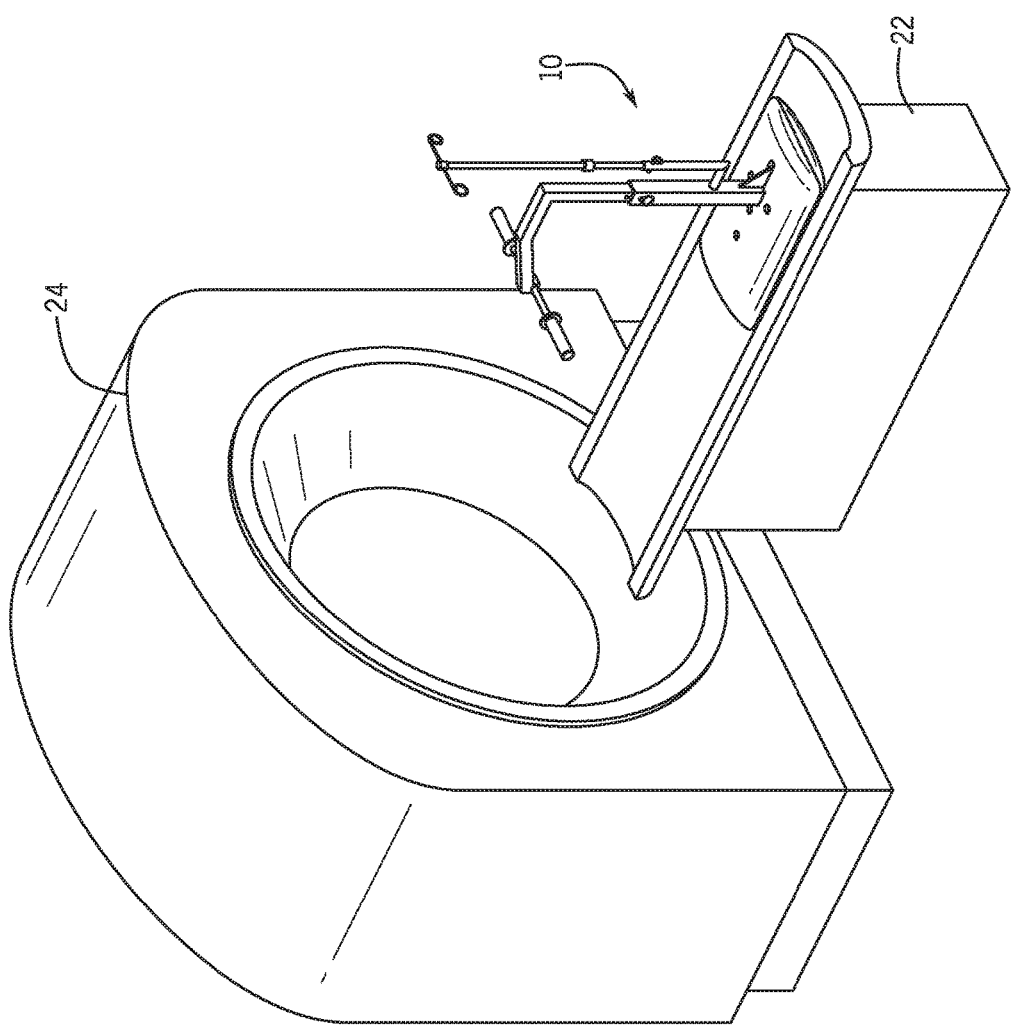

ARM SUPPORT SYSTEM

RELATED APPLICATION

This application claims priority to provisional patent application U.S. Ser. No. 62/296,794 filed on Feb. 18, 2016, the entire contents of which is herein incorporated by reference.

BACKGROUND

The embodiments herein relate generally to a medical device specifically, an arm support system to keep a patient's arm straight during administering IV fluids during a radiological procedure.

Prior to embodiments of the disclosed invention there were many difficulties in IV administration of fluids during the radiology procedures. For instance, the patient's arm and shoulder would be discomforted, the IV lines would become crimped, an air gap artifact could result and the patient's arm may not be straight throughout the procedure. Embodiments of the disclosed invention solve this problem.

SUMMARY

An arm support system is configured to hold a patient's arm straight during administration of IV fluids in a radiological procedure. The arm support system further includes a base attached to a plurality of straps for securing the base to a table or a bed with the plurality of straps. The base is further attached to an upright unit that, in turn, is attached to an IV upright member and to a right triangular support. Furthermore, a telescoping arm member and a telescoping IV member is attached to the upright member and the IV upright member, respectively. Then, the telescoping IV member is attached to a plurality of IV loops while the telescoping arm member is attached to a handle with a handle grip on both sides. A patient holds onto the handle grips that keeps the patient's arms straight while administrating IV during the radiological procedure.

BRIEF DESCRIPTION OF THE FIGURES

The detailed description of some embodiments of the invention is made below with reference to the accompanying figures, wherein like numerals represent corresponding parts of the figures.

FIG. 1 shows a perspective view of one embodiment of the present invention in use;

DETAILED DESCRIPTION OF CERTAIN EMBODIMENTS

Figure 3:
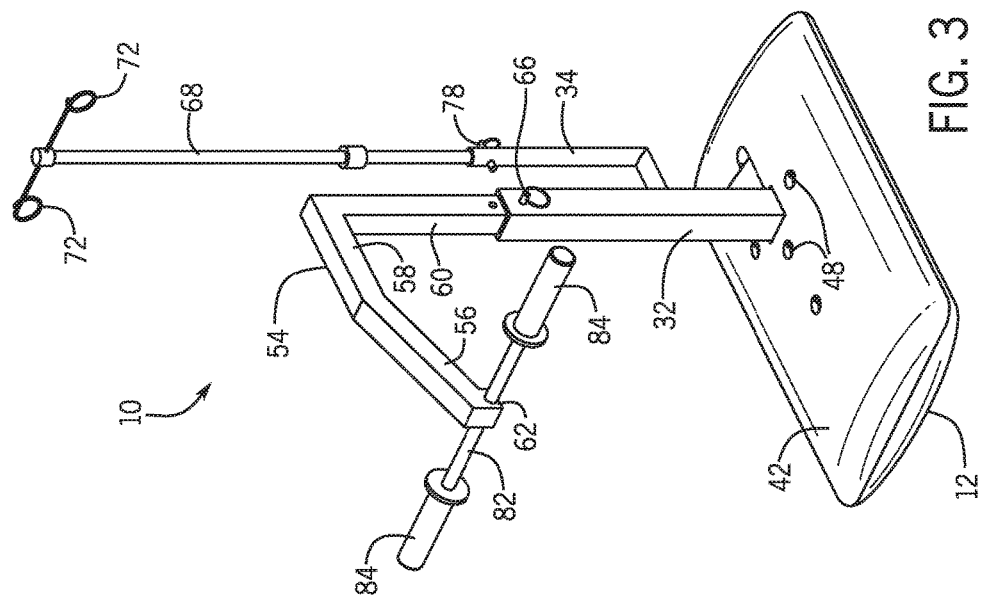
FIG. 3 shows a rear perspective view of one embodiment of the present invention.
Figure 2:
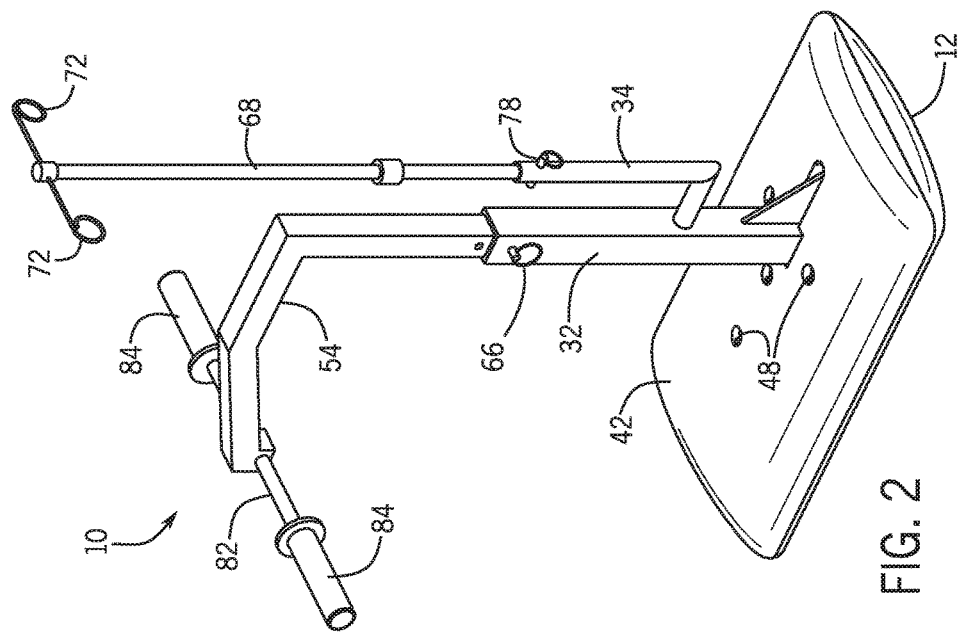
FIG. 2 shows a front view of one embodiment of the present invention.
Figure 4:
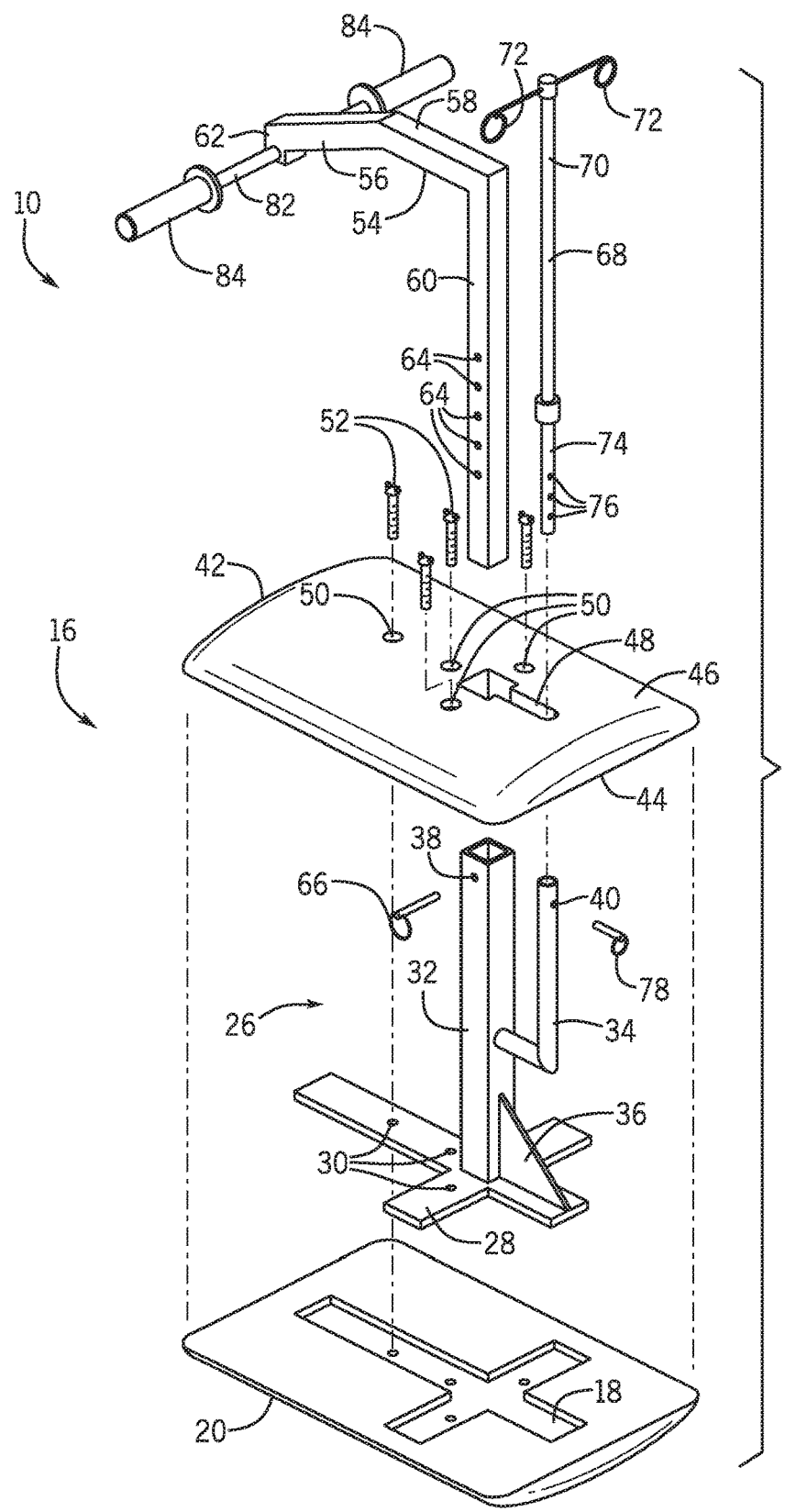
FIG. 4 shows an exploded view of one embodiment of the present invention.

By way of example, and referring to FIGS. 1-4, one embodiment of an arm support system is configured to hold a patient's arm straight during administration of IV fluids in a radiological procedure, such as a MRI scanner. The arm support system further comprises a base attached to a plurality of straps for securing the base to a table or a bed with the plurality of straps. The base is further attached to an upright unit that, in turn, is attached to an IV upright member and to a right triangular support. Furthermore, a telescoping arm member and a telescoping IV member is attached to the upright member and the IV upright member, respectively. Moreover, the telescoping IV member is attached to a plurality of IV loops while the telescoping arm member is attached to a handle having a handle grip on both sides. A patient holds onto the handle grips that keeps the patient's arms straight while administrating IV during the radiological procedure.

Now turning to details, and referring to FIGS. 1-4, one embodiment of the arm support system 10 comprises a base 12, having a bottom convex surface 14 and a top surface 16 with a cruciform depression 18. The base is attached to a plurality of straps 20 for securing the base to a table or a bed 22 that slides in a MM scanner 24 with the plurality of straps. Further, an upright unit 26 with a cruciform base 28 is configured to fit in the cruciform depression and further includes a plurality of openings 30. The upright unit further comprises an upright member 32 attached at a cross-section of the base, an IV upright member 34 attached to the upright member in middle and a right triangular support 36 attached to the upright member at base with both sides. The upright member is a square tube with a large pin opening 38 at end and the IV upright member is a cylindrical, L-shaped tube with a small pin opening 40. Furthermore, a base cover 42 with a bottom flat surface 44 and a top convex surface 46, comprises an opening for receiving the upright unit 48 except the cruciform base, and a plurality of openings 50 for receiving a plurality of mounting bolts 52 to securely hold the upright unit between the base and the base cover. The opening for receiving the upright unit further comprises a square opening merged with a slot and the square opening receives the upright member while the slot receives the IV upright member as well as the right triangular support. A telescoping arm member 54 is a square tube having a top portion 56, a middle portion 58 and a bottom portion 60 such that the bottom portion and the middle portion form right angle while the middle portion and the top portion form obtuse angle. The top portion comprises a handle opening 62 at end and the bottom portion is configured to nest within the upright member and comprises a plurality of height adjustment openings 64 for adjusting height by aligning one of the height adjustment openings with the large pin opening and then inserting a large pin 66 through the openings to lock. Next, a telescoping IV member 68 is cylindrical with a telescoping IV member top portion 70 attached to an IV loop 72 on both sides and a telescoping IV member bottom portion 74 is configured to nest within the IV upright member. The telescoping IV member bottom portion further comprises a plurality of telescoping IV member height adjustment openings 76 for adjusting height by aligning one of the telescoping IV member height adjustment openings with the small pin opening and then inserting a small pin 78 through the openings. Finally, a handle 80, having a tubular rod 82 is inserted through the handle opening and is attached to a handle grip 84 on both sides of the tubular rod for comfortably holding the handle that keeps the patient's arms straight while administrating IV during the radiological procedure.

Figure 5:
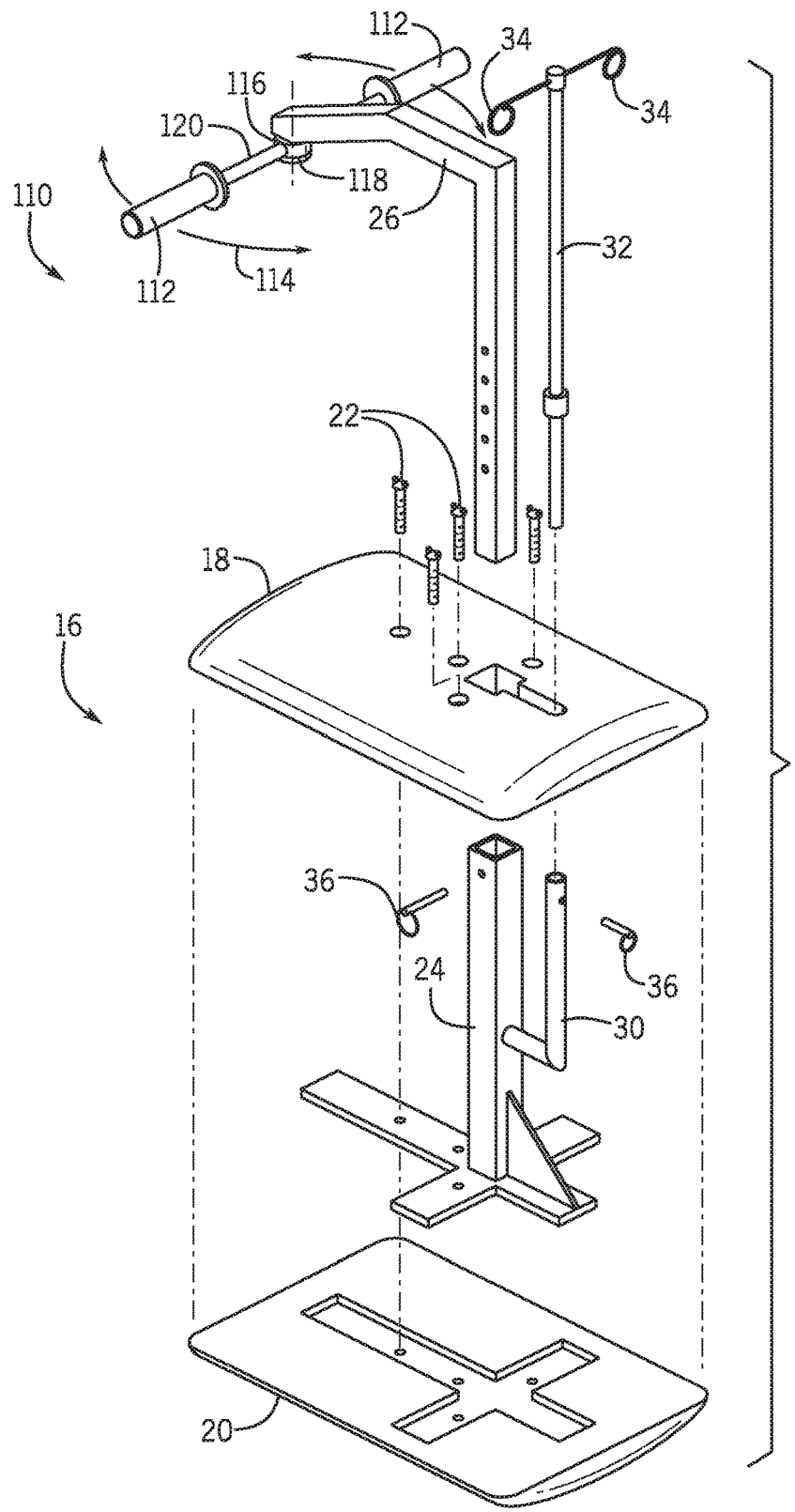
FIG. 5 shows a second embodiment of the present invention.

In a second embodiment 110 and referring to FIG. 5, the handle 112 of the arm support is configured to rotate in a horizontal plane 114. The handle opening 116 is attached to a pivot member 118 for receiving the tubular rod 120 that in turn enables the tubular rod to rotate.

The arm support is manufactured from sturdier and medically-approved materials, such as aluminium, fiberglass, laminate wood and industrial plastic. The plurality of straps are made of industrial plastic vinyl with heavy duty hook and loop closure. The base and the base cover are rectangular with the convex bottom surface and flat top surface and with dimensions of 16" width×24" length×2.25" height or 14" width×28" length×2.5" height. The cruciform depression has following dimensions: 0.5" depth, 2.75" width of each arm, 11.75" length of long arm, 19.25" total length of the cruciform. The opening for receiving the upright unit in the base cover comprises the square opening with 2.25" each side and the slot with 4" length and 1.25" height. The dimensions of the telescoping arm member are as follows: length of the top portion, the middle portion and the bottom portion are 8.75", 8" and 24" or 28.75", respectively while the diameter of the opening for receiving the handle at the end of the top portion is 1". The telescoping IV member is 16" long and 1.5" wide while distance between the two IV loops is 24". The upright unit comprises the cruciform base (19" long×2.5" wide each arm×12" long arm×5" short arm), the upright member (16.75" or 19" long), the L-shaped IV upright member (11" long arm×3.5" short arm and 1" diameter or 10"×4"×¾") and the right triangular support (9" hypotenuse).

As used in this application, the term "a" or "an" means "at least one" or "one or more."

As used in this application, the term "about" or "approximately" refers to a range of values within plus or minus 10% of the specified number.

As used in this application, the term "substantially" means that the actual value is within about 10% of the actual desired value, particularly within about 5% of the actual desired value and especially within about 1% of the actual desired value of any variable, element or limit set forth herein.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Any element in a claim that does not explicitly state "means for" performing a specified function, or "step for" performing a specified function, is not to be interpreted as a "means" or "step" clause as specified in 35 U.S.C. § 112, ¶6. In particular, any use of "step of" in the claims is not intended to invoke the provision of 35 U.S.C. § 112, ¶6.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. An arm support system, configured to hold a patient's arm straight during administration of IV fluids in a radiological procedure; the arm support system comprising:
    a base, having a bottom convex surface and a top surface with a cruciform depression, attached to a plurality of straps for securing the base with the plurality of straps;
    an upright unit, having a cruciform base configured to fit in the cruciform depression, an upright member attached at a cross-section of the base, an IV upright member attached to the upright member in middle and a right triangular support attached to the upright member at base with both sides,
    a base cover, having a bottom flat surface and a top convex surface, comprising an opening for receiving the upright unit except the cruciform base, and a plurality of openings for receiving a plurality of mounting bolts to securely hold the upright unit between the base and the base cover;
    a telescoping arm member, a square tube having a top, a middle portion and a bottom portion such that the bottom portion and the middle portion form right angle while the middle portion and the top portion form obtuse angle,
    a cylindrical telescoping IV member, having a telescoping IV member top portion attached to an IV loop on both sides and a telescoping IV member bottom portion configured to nest within the IV upright member, and
    a handle, having a tubular rod inserted through the handle opening and attached to a handle grip on both sides of the tubular rod for comfortably holding the handle that keeps the patient's arms straight while administrating IV during the radiological procedure.

2. The arm support system of claim 1,
    wherein the cruciform base further comprises a plurality of openings,
    wherein the upright member comprises a square tube with a large pin opening at end; and
    wherein the IV upright member comprises a cylindrical and L-shaped tube with a small pin opening.

3. The arm support system of claim 2, wherein the top portion comprised a handle opening at end and the bottom portion configured to nest within the upright member and comprised a plurality of height adjustment openings for adjusting height by aligning one of the height adjustment openings with the large pin opening and then inserting a large pin through the plurality of height adjustment openings.

4. The arm support system of claim 3, wherein the opening for receiving the upright unit further comprises a square opening merged with a slot and the square opening receives the upright member while the slot receives the IV upright member as well as the right triangular support.

5. The arm support system of claim 4, wherein the telescoping IV member bottom portion further comprised a plurality of telescoping IV member height adjustment openings for adjusting height by aligning one of the telescoping IV member height adjustment openings with the small pin opening and then inserting a small pin through the small pin opening.

6. The arm support system of claim 1,
    wherein the handle rotates in a horizontal plane; and
    wherein the handle opening is attached with a pivot member for receiving the tubular rod to enable the tubular rod to rotate.

* * * * *